United States Patent
Say

(10) Patent No.: US 9,044,178 B2
(45) Date of Patent: Jun. 2, 2015

(54) ELECTROCHEMICAL SENSOR AND METHOD FOR MANUFACTURING

(75) Inventor: James L. Say, Breckenridge, CO (US)

(73) Assignee: Pepex Biomedical, LLC, St. Louis, MO (US)

( * ) Notice: Subject to any disclaimer, the term of this patent is extended or adjusted under 35 U.S.C. 154(b) by 1261 days.

(21) Appl. No.: 12/674,876

(22) PCT Filed: Aug. 28, 2008

(86) PCT No.: PCT/US2008/074649
§ 371 (c)(1),
(2), (4) Date: May 3, 2011

(87) PCT Pub. No.: WO2009/051901
PCT Pub. Date: Apr. 23, 2009

(65) Prior Publication Data
US 2011/0203941 A1    Aug. 25, 2011

Related U.S. Application Data

(60) Provisional application No. 60/969,071, filed on Aug. 30, 2007.

(51) Int. Cl.
*G01N 27/327* (2006.01)
*A61B 5/145* (2006.01)
*A61B 5/1486* (2006.01)

(52) U.S. Cl.
CPC ........ *A61B 5/14532* (2013.01); *G01N 27/3272* (2013.01); *A61B 5/14865* (2013.01)

(58) Field of Classification Search
CPC ......... G01N 27/327–27/3272; A61B 5/14865; A61B 5/14532

USPC ............ 204/403.01–403.15; 205/777.5, 778, 205/792; 600/345–348
See application file for complete search history.

(56) References Cited

U.S. PATENT DOCUMENTS

| 1,454,224 | A | 5/1923 | Schmidt |
| 2,291,720 | A | 8/1942 | Hukle |
| 3,170,968 | A | 2/1965 | Rokunohe et al. |
| 3,823,035 | A | 7/1974 | Sanders |

(Continued)

FOREIGN PATENT DOCUMENTS

| DE | 10 112 384 | 9/2002 |
| DE | 10 2004 060 742 | 7/2006 |

(Continued)

OTHER PUBLICATIONS

European Search Report for 09826755.2 mailed Oct. 5, 2012.

(Continued)

*Primary Examiner* — J. Christopher Ball
*Assistant Examiner* — Maris R Kessel
(74) *Attorney, Agent, or Firm* — Merchant & Gould P.C.

(57) ABSTRACT

A sensor includes a sheath that is elongated along a longitudinal axis; a spacer positioned within the sheath and defining first and second channels having lengths that extend along the longitudinal axis; a first elongated member positioned within the first channel; and a second elongated member positioned within the second channel. The first elongated member includes an active surface forming a working electrode and the second elongated member including an active surface defining a counter electrode.

15 Claims, 13 Drawing Sheets

(56) References Cited

U.S. PATENT DOCUMENTS

| | | |
|---|---|---|
| 4,008,717 A | 2/1977 | Kowarski |
| 4,073,974 A | 2/1978 | Albarino et al. |
| 4,224,125 A | 9/1980 | Nakamura et al. |
| 4,255,487 A | 3/1981 | Sanders |
| 4,321,057 A | 3/1982 | Buckles |
| 4,399,099 A | 8/1983 | Buckles |
| 4,545,382 A | 10/1985 | Higgins et al. |
| 4,545,835 A | 10/1985 | Gusack et al. |
| 4,552,840 A | 11/1985 | Riffer |
| 4,573,968 A | 3/1986 | Parker |
| 4,640,821 A | 2/1987 | Mody et al. |
| 4,671,288 A | 6/1987 | Gough |
| 4,704,311 A | 11/1987 | Pickering et al. |
| 4,734,184 A | 3/1988 | Burleigh et al. |
| 4,762,603 A * | 8/1988 | Morin ............................ 228/135 |
| 4,820,399 A | 4/1989 | Senda et al. |
| 4,824,206 A | 4/1989 | Klainer et al. |
| 4,846,548 A | 7/1989 | Klainer |
| 4,880,752 A | 11/1989 | Keck et al. |
| 4,908,115 A | 3/1990 | Morita et al. |
| 4,919,649 A | 4/1990 | Timothy et al. |
| 4,927,516 A | 5/1990 | Yamaguchi et al. |
| 4,945,896 A | 8/1990 | Gade |
| 4,974,929 A | 12/1990 | Curry |
| 4,981,779 A | 1/1991 | Wagner |
| 5,001,054 A | 3/1991 | Wagner |
| 5,004,583 A | 4/1991 | Guruswamy et al. |
| RE33,677 E | 8/1991 | Vazirani |
| 5,047,044 A | 9/1991 | Smith et al. |
| 5,112,455 A | 5/1992 | Cozzette et al. |
| 5,131,138 A | 7/1992 | Crouse |
| 5,164,229 A | 11/1992 | Hay |
| 5,165,406 A | 11/1992 | Wong |
| 5,165,407 A | 11/1992 | Wilson et al. |
| 5,171,689 A | 12/1992 | Kawaguri et al. |
| 5,186,808 A | 2/1993 | Yamaguchi et al. |
| 5,205,920 A | 4/1993 | Oyama et al. |
| 5,217,533 A | 6/1993 | Hay et al. |
| 5,220,920 A | 6/1993 | Gharib |
| 5,243,982 A | 9/1993 | Möstl et al. |
| 5,244,636 A | 9/1993 | Walt et al. |
| 5,250,264 A | 10/1993 | Walt et al. |
| 5,262,035 A | 11/1993 | Gregg et al. |
| 5,264,092 A | 11/1993 | Skotheim et al. |
| 5,264,103 A | 11/1993 | Yoshioka et al. |
| 5,264,104 A | 11/1993 | Gregg et al. |
| 5,264,105 A | 11/1993 | Gregg et al. |
| 5,269,891 A * | 12/1993 | Colin ......................... 205/777.5 |
| 5,271,815 A | 12/1993 | Wong |
| 5,271,820 A | 12/1993 | Kinlen et al. |
| 5,277,872 A | 1/1994 | Bankert et al. |
| 5,298,144 A | 3/1994 | Spokane |
| 5,298,741 A | 3/1994 | Walt et al. |
| 5,320,725 A | 6/1994 | Gregg et al. |
| 5,320,814 A | 6/1994 | Walt et al. |
| 5,330,634 A | 7/1994 | Wong et al. |
| 5,356,786 A | 10/1994 | Heller et al. |
| 5,366,527 A | 11/1994 | Amos et al. |
| 5,372,133 A | 12/1994 | Hogen Esch |
| D354,347 S | 1/1995 | Knute et al. |
| D354,559 S | 1/1995 | Knute et al. |
| 5,384,028 A | 1/1995 | Ito |
| 5,422,246 A | 6/1995 | Koopal et al. |
| 5,431,174 A | 7/1995 | Knute |
| 5,437,973 A | 8/1995 | Vadgama et al. |
| 5,503,728 A | 4/1996 | Kaneko et al. |
| 5,505,828 A | 4/1996 | Wong et al. |
| 5,512,159 A | 4/1996 | Yoshioka et al. |
| 5,575,403 A | 11/1996 | Charlton et al. |
| 5,593,852 A | 1/1997 | Heller et al. |
| 5,605,152 A | 2/1997 | Slate et al. |
| 5,609,749 A | 3/1997 | Yamauchi et al. |
| 5,645,710 A | 7/1997 | Shieh |
| 5,656,241 A | 8/1997 | Seifert et al. |
| 5,720,924 A | 2/1998 | Eikmeier et al. |
| 5,810,199 A | 9/1998 | Charlton et al. |
| 5,849,415 A | 12/1998 | Shalaby et al. |
| 5,863,800 A | 1/1999 | Eikmeier et al. |
| 5,900,215 A | 5/1999 | Seifert et al. |
| 5,951,764 A | 9/1999 | Hay et al. |
| 5,971,941 A | 10/1999 | Simons et al. |
| 5,972,199 A | 10/1999 | Heller et al. |
| 5,982,959 A | 11/1999 | Hopenfeld |
| 5,997,501 A | 12/1999 | Gross et al. |
| 6,036,924 A | 3/2000 | Simons et al. |
| 6,044,665 A | 4/2000 | Lysson et al. |
| 6,048,352 A | 4/2000 | Douglas et al. |
| D424,696 S | 5/2000 | Ray et al. |
| D426,638 S | 6/2000 | Ray et al. |
| 6,071,294 A | 6/2000 | Simons et al. |
| 6,071,391 A | 6/2000 | Gotoh et al. |
| 6,083,710 A | 7/2000 | Heller et al. |
| 6,103,199 A | 8/2000 | Bjornson et al. |
| 6,107,083 A | 8/2000 | Collins et al. |
| 6,120,676 A | 9/2000 | Heller et al. |
| 6,143,164 A | 11/2000 | Heller et al. |
| 6,241,863 B1 | 6/2001 | Monbouquette |
| 6,299,757 B1 | 10/2001 | Feldman et al. |
| 6,329,161 B1 | 12/2001 | Heller et al. |
| 6,338,790 B1 | 1/2002 | Feldman et al. |
| 6,379,317 B1 | 4/2002 | Kintzig et al. |
| 6,461,496 B1 | 10/2002 | Feldman et al. |
| 6,464,849 B1 | 10/2002 | Say et al. |
| 6,503,381 B1 | 1/2003 | Gotoh et al. |
| 6,560,471 B1 | 5/2003 | Heller et al. |
| 6,561,989 B2 | 5/2003 | Whitson |
| 6,576,101 B1 | 6/2003 | Heller et al. |
| 6,591,125 B1 | 7/2003 | Buse et al. |
| 6,592,745 B1 | 7/2003 | Feldman et al. |
| 6,607,658 B1 | 8/2003 | Heller et al. |
| 6,610,978 B2 | 8/2003 | Yin et al. |
| 6,616,819 B1 | 9/2003 | Liamos et al. |
| 6,618,934 B1 | 9/2003 | Feldman et al. |
| 6,620,112 B2 | 9/2003 | Klitmose |
| 6,676,816 B2 | 1/2004 | Mao et al. |
| 6,706,159 B2 | 3/2004 | Moerman et al. |
| 6,707,554 B1 | 3/2004 | Miltner et al. |
| 6,740,214 B1 | 5/2004 | Dobson et al. |
| 6,749,740 B2 | 6/2004 | Liamos et al. |
| 6,783,502 B2 | 8/2004 | Orloff et al. |
| 6,840,912 B2 | 1/2005 | Kloepfer et al. |
| 6,881,551 B2 | 4/2005 | Heller et al. |
| 6,893,545 B2 | 5/2005 | Gotoh et al. |
| 6,965,791 B1 | 11/2005 | Hitchcock et al. |
| 7,008,799 B1 | 3/2006 | Zimmer et al. |
| 7,058,437 B2 | 6/2006 | Buse et al. |
| 7,211,437 B2 | 5/2007 | Schabbach et al. |
| 7,264,139 B2 | 9/2007 | Brickwood et al. |
| 7,282,705 B2 | 10/2007 | Brennen |
| 7,299,081 B2 | 11/2007 | Mace et al. |
| 7,322,942 B2 | 1/2008 | Roe |
| 7,335,294 B2 | 2/2008 | Heller et al. |
| 7,344,499 B1 | 3/2008 | Prausnitz et al. |
| 7,378,007 B2 | 5/2008 | Moerman et al. |
| 7,396,334 B2 | 7/2008 | Kuhr et al. |
| 7,585,278 B2 | 9/2009 | Aceti et al. |
| 7,723,099 B2 | 5/2010 | Miller et al. |
| 7,740,581 B2 | 6/2010 | Buse et al. |
| 7,828,749 B2 | 11/2010 | Douglas et al. |
| 7,829,023 B2 | 11/2010 | Burke et al. |
| 7,860,544 B2 | 12/2010 | Say et al. |
| 2002/0040208 A1 | 4/2002 | Flaherty et al. |
| 2002/0098124 A1 | 7/2002 | Bentsen et al. |
| 2004/0087033 A1 | 5/2004 | Schembri |
| 2004/0102717 A1 | 5/2004 | Qi |
| 2004/0236251 A1 | 11/2004 | Roe et al. |
| 2005/0023137 A1 | 2/2005 | Bhullar et al. |
| 2005/0067737 A1 | 3/2005 | Rappin et al. |
| 2005/0089944 A1 | 4/2005 | Shieh et al. |
| 2005/0196747 A1 | 9/2005 | Stiene |
| 2005/0197548 A1 | 9/2005 | Dietiker |
| 2006/0241517 A1 | 10/2006 | Fowler et al. |
| 2007/0149897 A1 | 6/2007 | Ghesquiere et al. |
| 2007/0199818 A1 | 8/2007 | Petyt et al. |

(56) References Cited

U.S. PATENT DOCUMENTS

| | | |
|---|---|---|
| 2008/0017645 A1 | 1/2008 | Garagiola |
| 2008/0097546 A1 | 4/2008 | Powers et al. |
| 2008/0167578 A1 | 7/2008 | Bryer et al. |
| 2009/0021901 A1 | 1/2009 | Stothers |
| 2009/0032760 A1 | 2/2009 | Muscatell |
| 2009/0069654 A1 | 3/2009 | Yasuzawa et al. |
| 2009/0178923 A1* | 7/2009 | Marquant et al. ........ 204/403.01 |
| 2009/0257917 A1 | 10/2009 | Nakamura et al. |
| 2010/0018869 A1 | 1/2010 | Feldman et al. |
| 2010/0018871 A1 | 1/2010 | Feldman et al. |
| 2010/0051479 A1 | 3/2010 | Heller et al. |
| 2010/0059372 A1 | 3/2010 | Heller et al. |
| 2010/0059373 A1 | 3/2010 | Heller et al. |
| 2010/0072063 A1 | 3/2010 | Heller et al. |
| 2010/0072064 A1 | 3/2010 | Heller et al. |
| 2010/0326842 A1 | 12/2010 | Mazza et al. |
| 2011/0028815 A1 | 2/2011 | Simpson et al. |
| 2011/0086373 A1 | 4/2011 | Wallace-Davis et al. |
| 2011/0189762 A1 | 8/2011 | Say |
| 2011/0203941 A1 | 8/2011 | Say |
| 2011/0265944 A1 | 11/2011 | Say |
| 2011/0266149 A1 | 11/2011 | Say |
| 2011/0270061 A1 | 11/2011 | Say |
| 2012/0291254 A1 | 11/2012 | Say |

FOREIGN PATENT DOCUMENTS

| | | |
|---|---|---|
| EP | 0 256 415 A2 | 2/1988 |
| EP | 0 327 658 A1 | 8/1989 |
| EP | 0 409 033 A2 | 1/1991 |
| EP | 0 420 296 A1 | 4/1991 |
| EP | 0 592 805 A2 | 4/1994 |
| EP | 0 710 835 A2 | 5/1996 |
| EP | 0 792 620 A2 | 9/1997 |
| EP | 0 965 301 A1 | 12/1999 |
| EP | 1 462 775 B1 | 12/2007 |
| JP | 64-3552 | 1/1989 |
| JP | 1-153952 | 6/1989 |
| JP | 1-263537 | 10/1989 |
| JP | 4-279854 | 10/1992 |
| JP | 6-174946 | 6/1994 |
| JP | 8-107890 | 4/1996 |
| JP | 2007-202632 | 8/2007 |
| WO | WO 89/07139 | 8/1989 |
| WO | WO 91/15993 | 10/1991 |
| WO | WO 94/10553 | 5/1994 |
| WO | WO 96/22730 | 8/1996 |
| WO | WO 96/39616 | 12/1996 |
| WO | WO 97/15827 | 5/1997 |
| WO | WO 00/35340 | 6/2000 |
| WO | WO 2005/051183 A1 | 6/2005 |
| WO | WO 2007/091633 A1 | 8/2007 |
| WO | WO 2008/017645 A1 | 2/2008 |
| WO | WO2009/032760 | 3/2009 |
| WO | WO 2009/051901 A2 | 4/2009 |
| WO | WO 2010/056869 A2 | 5/2010 |
| WO | WO 2010/056876 A2 | 5/2010 |
| WO | WO 2010/056878 A2 | 5/2010 |

OTHER PUBLICATIONS

International Search Report and Written Opinion for PCT/US2008/074649 mailed Apr. 20, 2009.

International Search Report and Written Opinion for PCT/US2008/074644 mailed May 14, 2009.

International Search Report and Written Opinion for PCT/US2009/064216 mailed May 3, 2010.

International Search Report and Written Opinion for PCT/US2009/064225 mailed May 4, 2010.

International Search Report and Written Opinion for PCT/US2009/064228 mailed Jul. 1, 2010.

Jaraba et al., "NADH amperometric sensor based on poly(3-methylthiophene)-coated cylindrical carbon fiber microelectrodes: application to the enzymatic determination of L-lactate," *Electrochimica Acta*. (1998) 43 (23): 3555-3565.

Netchiporouk et al., "Properties of carbon fibre microelectrodes as a basis for enzyme biosensors," *Analytica Chimica Acta* (1995) 303: 275-283.

Sakslund et al, "Analysis of the factors determining the sensitivity of a miniaturized glucose biosensor made by codeposition of palladium and glucose oxidase onto an 8 μm carbon filter," *Journal of Electroanalytical Chemistry* (1996) 402: 149-160.

Sakslund et al., "Development and evaluation of glucose microsensors based on electrochemical codeposition of ruthenium and glucose oxidase onto carbon fiber microelectrodes," *Journal of Electroanalytical Chemistry* (1995) 397: 149-155.

* cited by examiner

ELECTROCHEMICAL SENSOR AND METHOD FOR MANUFACTURING

This application is a National Stage Application of PCT/US2008/074649, filed on Aug. 28, 2008, which claims the benefit of U.S. Provisional patent application Ser. No. 60/969,071, filed Aug. 30, 2007. To the extent appropriate, a claim of priority is made to each of the above disclosed applications.

TECHNICAL FIELD

The present disclosure relates to sensors for measuring bioanalytes and to methods for making such sensors.

BACKGROUND

Electrochemical bio-sensors have been developed for detecting analyte concentrations in a given fluid sample. For example, U.S. Pat. Nos. 5,264,105; 5,356,786; 5,262,035; 5,320,725; and 6,464,849, which are hereby incorporated by reference in their entireties, disclose wired enzyme sensors for detecting analytes such as lactate or glucose. Technology adapted for enhancing sensor miniaturization, cost effectiveness and durability is desirable.

SUMMARY

One aspect of the present disclosure relates to an electrochemical sensor including a first elongated member having an active surface defining a working electrode, a second elongated member having an active surface defining a counter electrode and a third elongated member having an active surface defining a reference electrode. The working electrode is covered with a sensing layer. The first, second and third elongated members have lengths that extend longitudinally through an insulator sheath. A spacer member is positioned within the insulator sheath for separating the first, second and third elongated members. The spacer member defines a first longitudinal channel for receiving the first elongated member, a second longitudinal channel for receiving the second elongated member and a third elongate channel for receiving the third elongated member. In use, the active surfaces are adapted to contact a sample desired to be tested.

Another aspect of the present disclosure relates to an electrochemical sensor including a first elongated member having an active surface defining a working electrode and a second elongated member having an active surface defining a counter/reference electrode. The working electrode is covered with a sensing layer. The first and second elongated members have lengths that extend longitudinally through an insulator sheath. A spacer member is positioned within the insulator sheath for separating the first and second elongated members. The spacer member defines a first longitudinal channel for receiving the first elongated member and a second longitudinal channel for receiving the second elongated member. In use, the active surfaces are adapted to contact a sample desired to be tested.

A further aspect of the present disclosure relates to an electrochemical sensor including an elongated member including at least an outer portion that is conductive. The elongated member is encased within a sheath defining a plurality of side openings that extend through a thickness of the sheath. A sensing material is positioned within the side openings.

A variety of additional inventive aspects will be set forth in the description that follows. The inventive aspects can relate to individual features and to combinations of features. It is to be understood that both the foregoing general description and the following detailed description are exemplary and explanatory only and are not restrictive of the broad inventive concepts upon which the embodiments disclosed herein are based.

DETAILED DESCRIPTION

Figure 1:
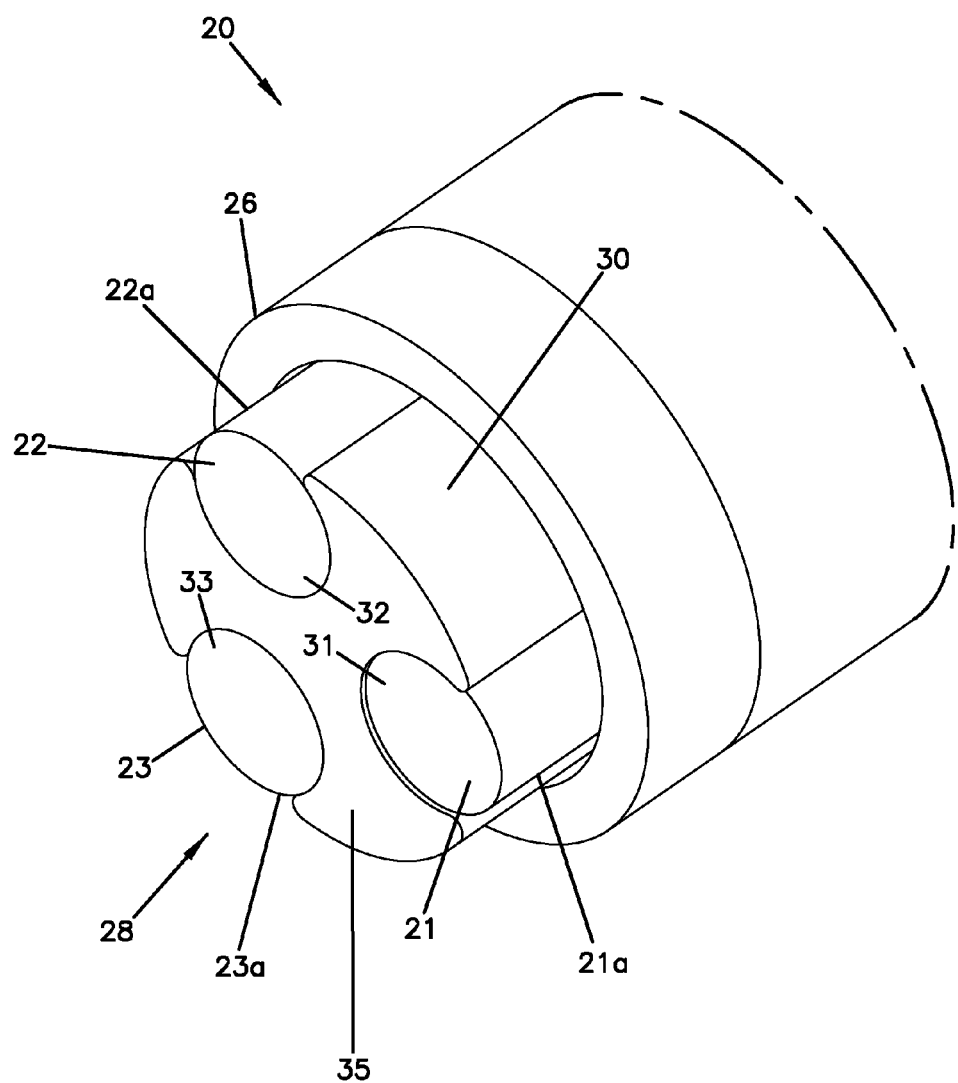
FIG. 1 is a perspective view showing a sensing tip of a first sensor having features that are examples of inventive aspects in accordance with the principles of the present disclosure.

Reference will now be made in detail to exemplary aspects of the present disclosure which are illustrated in the accompanying drawings. Wherever possible, the same reference numbers will be used throughout the drawings to refer to the same or like parts.

The following definitions are provided for terms used herein:

A "working electrode" is an electrode at which the analyte (or a second compound whose level depends on the level of the analyte) is electrooxidized or electroreduced with or without the agency of an electron transfer agent.

A "reference electrode" is an electrode used in measuring the potential of the working electrode. The reference electrode should have a generally constant electrochemical potential as long as no current flows through it. As used herein, the term "reference electrode" includes pseudo-reference electrodes. In the context of the disclosure, the term "reference electrode" can include reference electrodes which also function as counter electrodes (i.e., a counter/reference electrode).

A "counter electrode" refers to an electrode paired with a working electrode to form an electrochemical cell. In use, electrical current passes through the working and counter electrodes. The electrical current passing through the counter electrode is equal in magnitude and opposite in sign to the current passing through the working electrode. In the context of the disclosure, the term "counter electrode" can include counter electrodes which also function as reference electrodes (i.e., a counter/reference electrode).

A "counter/reference electrode" is an electrode that functions as both a counter electrode and a reference electrode.

An "electrochemical sensing system" is a system configured to detect the presence and/or measure the level of an analyte in a sample via electrochemical oxidation and reduction reactions on the sensor. These reactions are transduced to an electrical signal that can be correlated to an amount, concentration, or level of an analyte in the sample. Further details about electrochemical sensing systems, working electrodes, counter electrodes and reference electrodes can be found at U.S. Pat. No. 6,560,471 that is hereby incorporated by reference in its entirety.

"Electrolysis" is the electrooxidation or electroreduction of a compound either directly at an electrode or via one or more electron transfer agents.

An "electron transfer agent" is a compound that carries electrons between the analyte and the working electrode, either directly, or in cooperation with other electron transfer agents. One example of an electron transfer agent is a redox mediator.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both. In some embodiments, the sensing layer has a generally dry or non-hydrated state prior to use. In such embodiments, the sensing layer can be hydrated during use by water within the fluid sample being tested.

Figure 2:
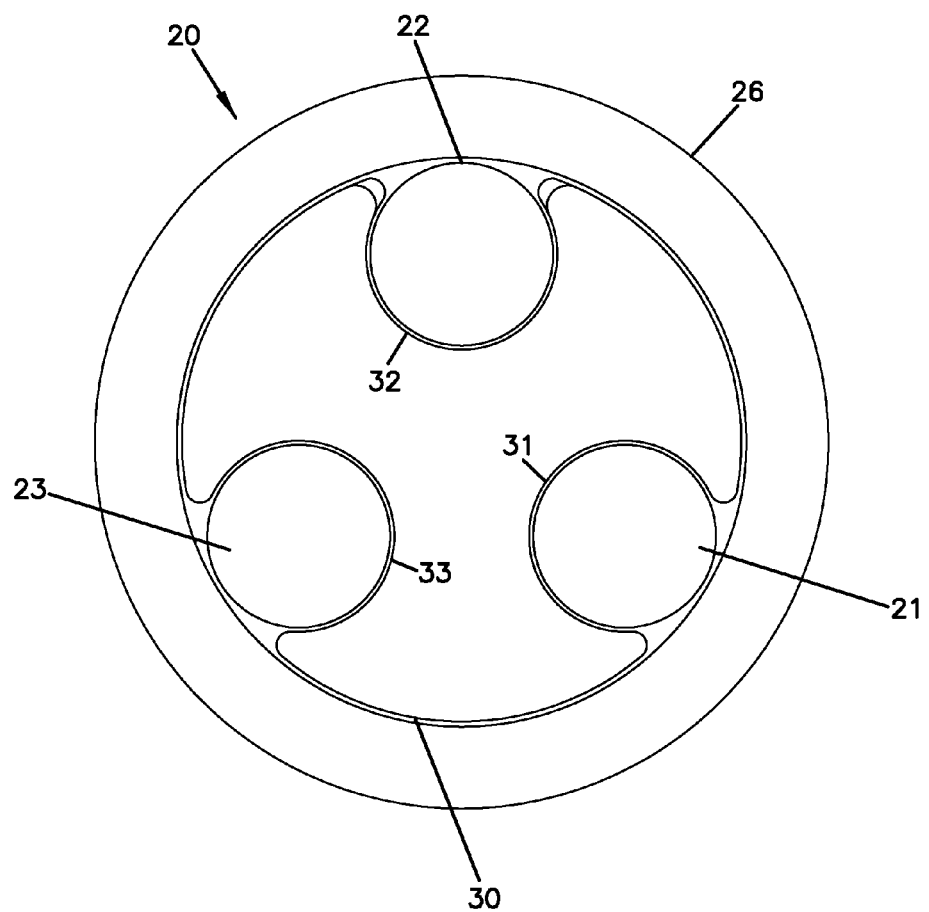
FIG. 2 is an end view showing the sensing tip of the sensor of FIG. 1.
Figure 3:
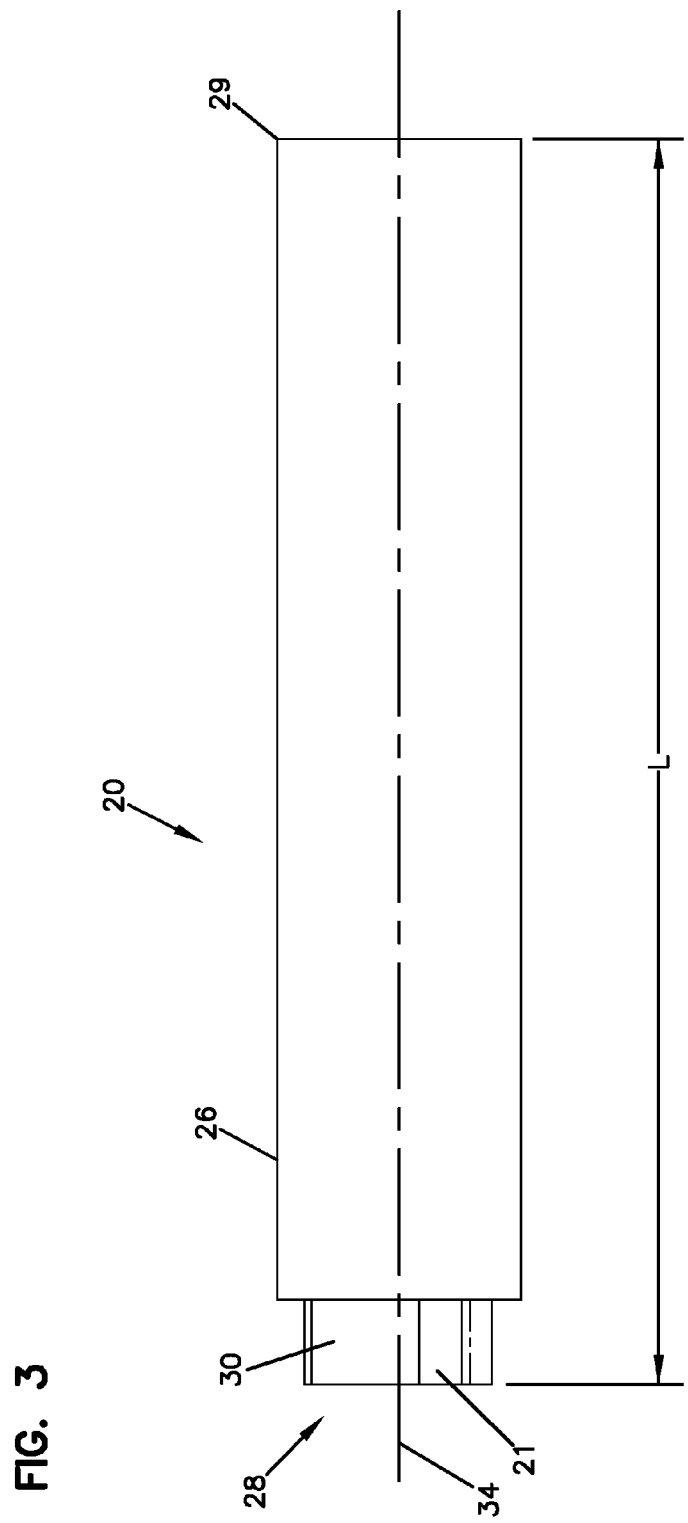
FIG. 3 is a side view of the sensor of FIG. 1.
Figure 4:
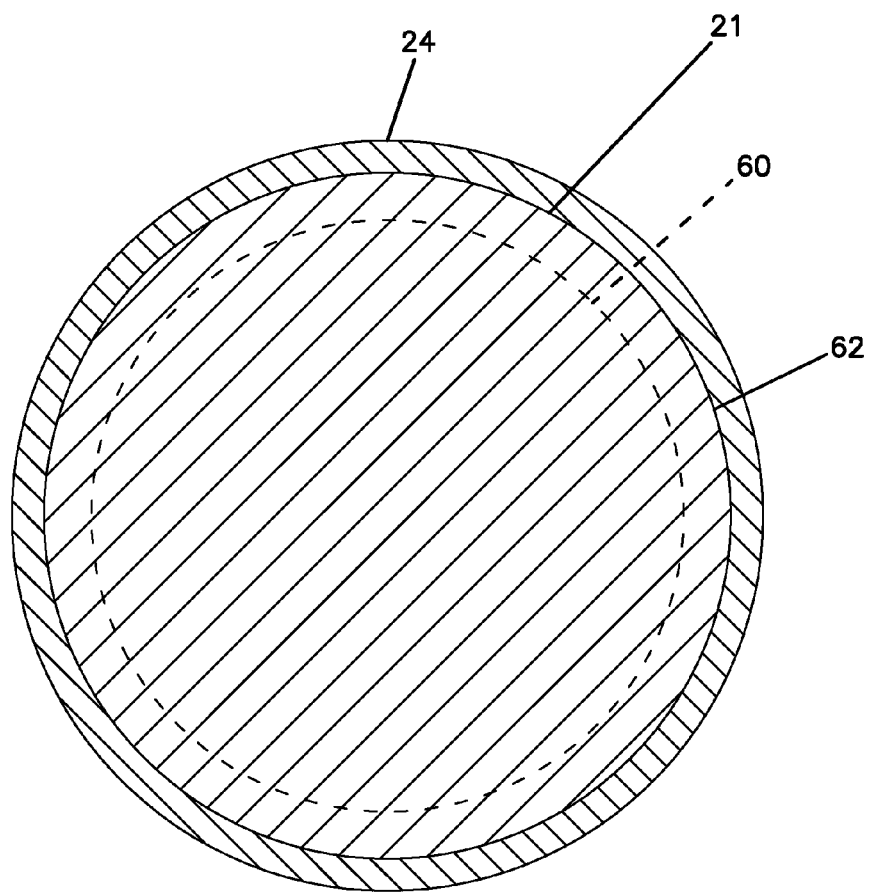
FIG. 4 is a transverse cross-sectional view of a fiber used within the sensor of FIG. 1 as a working electrode, the fiber is shown covered with a layer of sensing chemistry.

FIGS. 1-3 illustrate a sensor 20 having features that are examples of inventive aspects in accordance with the principles of the present disclosure. The sensor 20 includes first, second and third elongated members 21, 22 and 23 each having at least a portion that is electrically conductive. An insulating layer 26 surrounds the first, second and third elongated members 21, 22 and 23. The sensor 20 includes a sensing tip 28 at which active surfaces 21a, 22a and 23a of the first, second and third elongated members 21, 22 and 23 project beyond the insulating layer 26. The first elongated member 21 functions as a working electrode and includes a sensing layer 24 (see FIG. 4) that is positioned at least at the active end of the first elongated member 21. The second and third elongated members 22, 23 function respectively as counter and reference electrodes. The sensor 20 also includes a base end 29 positioned opposite from the sensing tip 28. The elongated members 21-23 can extend from the sensing tip 28 to the base end 29. A length L of the sensor 20 extends from the sensing tip 28 to the base end 29. In one embodiment, the length L is in the range of 20-40 centimeters.

Referring to FIGS. 1 and 3, the sensor 20 includes a spacer 30 positioned within the insulating layer 26 for separating the elongated members 21-23. The spacer is preferably constructed of a dielectric material and includes first, second and third channels 31-33 that are parallel and that extend through along a longitudinal axis 34 of the sensor generally from the sensing tip 28 to the base end 29. The first, second and third channels 31-33 respectively receive the first, second and third elongated members 21-23. As shown at FIG. 1, distal ends of the first, second and third elongated members 21-23 are generally flush with a distal end 35 of the spacer 30. In other embodiments, the distal ends of the elongated members 21-23 project outwardly beyond the distal end 35 of the spacer 30. In one embodiment, the spacer has an extruded polymer construction.

Referring to FIG. 1, the active surfaces 21a, 22a, and 23a of the elongated members 21-23 face radially outwardly from the channels 31-33 and are exposed (i.e., not covered by the spacer 30). Radially inwardly facing surfaces 21b, 22b and 23b of the elongated members 21-23 are covered by the spacer 30. The insulating layer 26 covers the radially outwardly facing portions of the elongated members 21-23 that do not project beyond the insulating layer 26. In this way, the insulating layer 26 and the spacer 30 control the sizes of the active surfaces 21a, 22a and 23a. In other words, the insulating layer 26 and the spacer 30 are configured to ensure that only the active surfaces 21a, 22a and 23a are exposed to an analyte desired to be sensed within a test sample.

Figure 6:
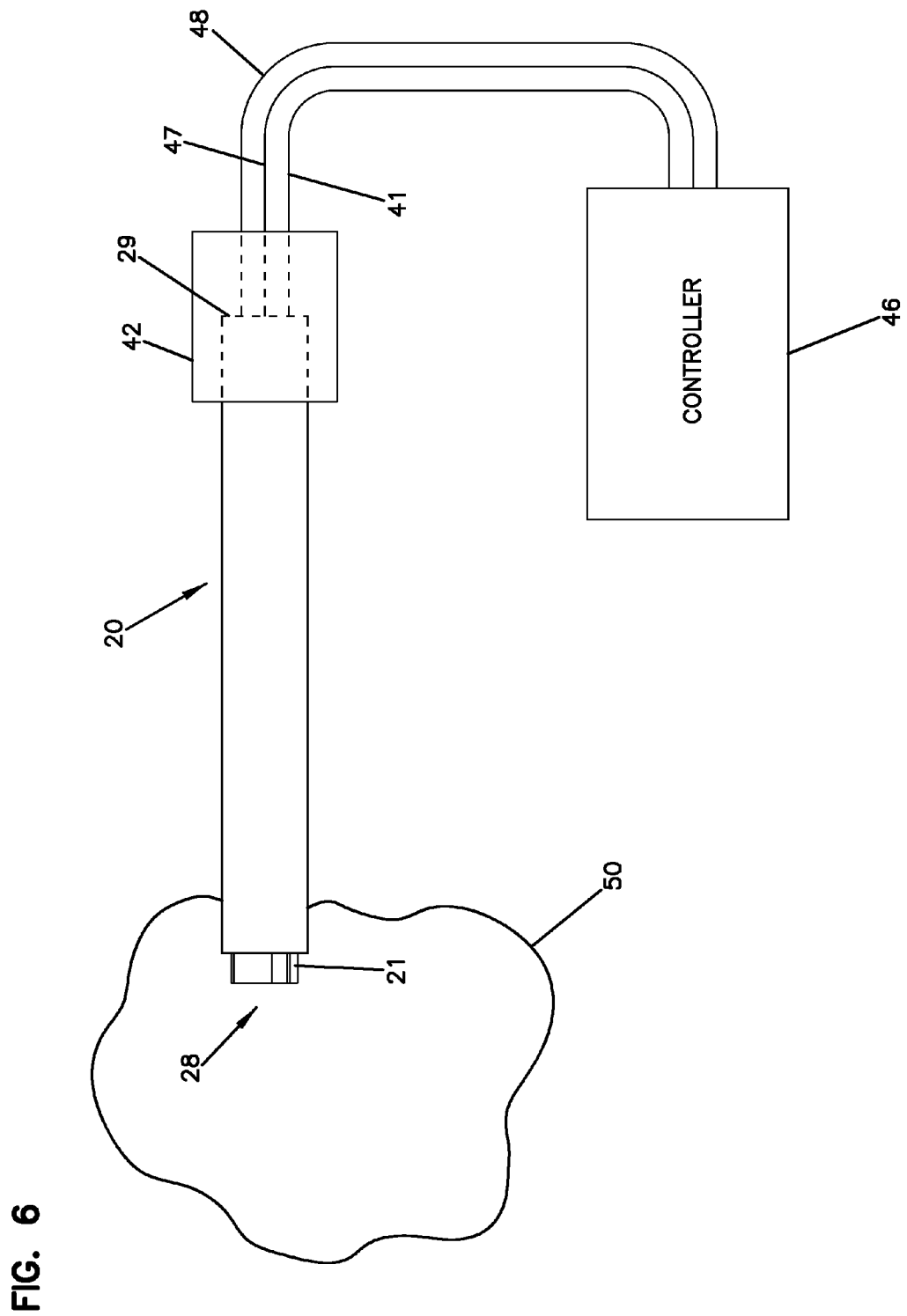
FIG. 6 is a schematic view of a sensor system incorporating the sensor of FIG. 1.

FIG. 6 illustrates an electrochemical sensing system 40 that incorporates the sensor 20 of FIGS. 1-3. The working electrode of the elongated member 21 is electrically connected to a wire 41 by a connector or hub 42 positioned at the base end 29 of the sensor 20. The wire 41 electrically connects the working electrode of the elongated member 21 to a controller 46. The controller 46 can be any type of controller such as a micro-controller, a mechanical controller, a software driven controller, a hardware driven controller, a firmware driven controller, etc. The controller can include a microprocessor that interfaces with memory. The hub 42 also electrically connects the second and third elongated members 22, 23 to wires 47, 48 routed to the controller 46. In this way, the reference and counter electrodes are also electrically connected to the controller 46.

In use of the sensing system 40, the sensing tip 28 of the sensor 20 is immersed within a test volume 50 of a liquid sample (e.g., a blood sample) containing an analyte desired to be sensed. The sample may be an ex vivo or in vivo sample. With the sensor 20 so positioned, water within the test volume 50 can diffuse into the sensing layer 24 at the active tip of the working electrode such that the sensing layer 24 is hydrated. The analyte within the test volume 50 also diffuses into the sensing layer 24. A voltage potential is then applied between the counter electrode (i.e., the second elongated member 22) and the working electrode (i.e., the first elongated member 21). The reference electrode (i.e., the third elongated member 23) assists in measuring the voltage potential between the working and counter electrodes. When the potential is applied, an electrical current will flow through the test volume 50 between the counter electrode and the working electrode. The current is a result of the oxidation or reduction of the analyte in the test volume 50. This electrochemical reaction occurs via the electron transfer agent in the sensing layer 24 and the optional electron transfer catalyst/enzyme in the sensing layer 24. By measuring the current flow generated at a given potential, the concentration of a given analyte in the test sample can be determined. Those skilled in the art will recognize that current measurements can be obtained by a variety of techniques including, among other things, coulometric, potentiometric, amperometric, voltammetric, and other electrochemical techniques.

Figure 5:
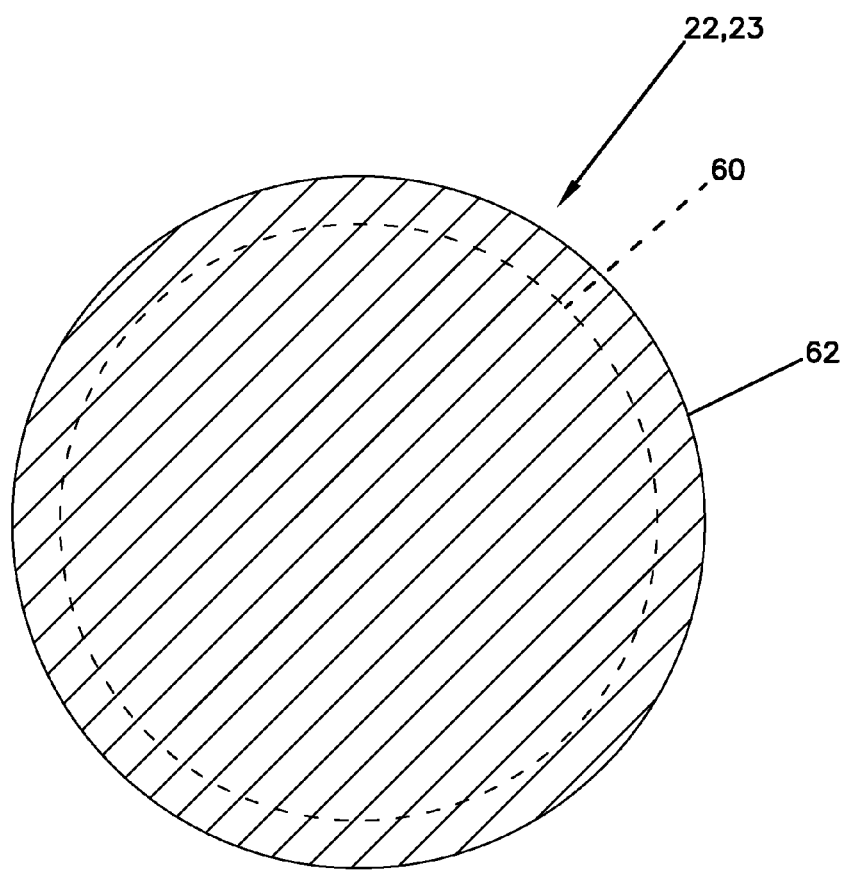
FIG. 5 is a transverse cross-sectional view of a fiber used within the sensor of FIG. 1 as a counter or reference electrode.

In certain embodiments, the elongated members 21-23 of the sensor 20 can each include an electrically conductive wire or fiber. For example, the elongated members 21-23 can each include a metal wire or a glassy carbon fiber. In a preferred embodiment, the elongated members 21-23 have a composite structure and each includes a fiber having a dielectric core 60 surrounded by a conductive layer 62. In the case of the first elongated member 21, the conductive layer 62 is covered by the sensing layer 24 (see FIG. 4) and functions as a working electrode. In the case of the second and third elongated members 22, 23 (see FIG. 5 which is representative of both the first and second elongated members 22, 23), the conductive layers 62 are not covered with a sensing layer. For the elongated members 22, 23, the conductive layers 62 function as the counter and reference electrodes, respectively.

A preferred composite fiber for constructing the elongated members 21-23 is sold under the name Resistat® by Shakespeare Conductive Fibers LLC. This composite fiber includes a composite nylon monofilament conductive thread material made conductive by the suffusion of about a 1 micron layer of carbonized nylon isomer onto a dielectric nylon core material. The Resistat® material is comprised of isomers of nylon to create the basic 2 layer composite thread. However, many other polymers are available for the construction such as: polyethylene terephthalate, nylon 6, nylon 6,6, cellulose, polypropylene cellulose acetate, polyacrylonitrile and copolymers of polyacrylonitrile for a first component and polymers such as of polyethylene terephthalate, nylon 6, nylon 6,6, cellulose, polypropylene cellulose acetate, polyacrylonitrile and copolymers of polyacrylonitrile as constituents of a second component. Inherently conductive polymers (ICP) such as doped polyanaline or polypyrrole can be incorporated into the conductive layer along with the carbon to complete the formulation. In certain embodiments, the ICP can be used as the electrode surface alone or in conjunction with carbon. The Resistat® fiber product is currently sold with a circular transverse cross-sectional profile. By post forming or extruding the Resistat® fiber, other transverse cross-sectional profiles (e.g., generally triangular) can be provided. The Resistat® fiber is available in diameters of 0.0025 to 0.016 inches, which as suitable for sensors in accordance with the principles of the present disclosure. Example patents disclosing composite fibers suitable for use in practicing sensors in accordance with the principles of the present disclosure include U.S. Pat. Nos. 3,823,035; 4,255,487; 4,545,835 and 4,704,311, which are incorporated herein by reference.

The sensing layer 24 preferably includes a sensing chemistry such as a redox compound or mediator. The term redox compound is used herein to mean a compound that can be oxidized or reduced. Exemplary redox compounds include transition metal complexes with organic ligands. Preferred redox compounds/mediators are osmium transition metal complexes with one or more ligands having a nitrogen containing heterocycle such as 2,2'-bipyridine. The sensing material can also include a redox enzyme. A redox enzyme is an enzyme that catalyzes an oxidation or reduction of an analyte. For example, a glucose oxidase or glucose dehydrogenase can be used when the analyte is glucose. Also, a lactate oxidase or lactate dehydrogenase fills this role when the analyte is lactate. In systems such as the one being described, these enzymes catalyze the electrolysis of an analyte by transferring electrons between the analyte and the electrode via the redox compound. Further information regarding sensing chemistry can be found at U.S. Pat. Nos. 5,264,105; 5,356,786; 5,262,035; and 5,320,725, which were previously incorporated by reference in their entireties.

The insulating layer 26 of the sensor 20 preferably serves numerous functions to the sensor 20. For example, the insulating layer 26 preferably electrically insulates the elongated members 21-23. Additionally, the insulating layer 26 preferably provides mechanical strength for protecting the elongated members 21-23. In one nonlimiting embodiment, the insulating layer 26 is made of a polymeric material such as polyimide, polyurethane or other materials. In certain embodiments, the insulating layer 26 can have a maximum outer dimension (e.g., an outer diameter) less than 2 millimeters. The insulating layer 26 may be an off shelf shrink component, a co-extruded, extruded or injection molded component serving the purposes of defining the available surface area of the electrodes accessible by the analyte and insulating the inactive portion of the elongated members in order for it to provide a conductive link from the active portions of the elongated members back to the hub 42 or to another structure such as an alternative type of terminal connector, a display or a wireless node.

It will be appreciated that the sensor 20 can be used for ex vivo or in vivo applications. In certain embodiments, the sensor 20 can be incorporated into a peripheral catheter to provide on-line monitoring of bioanalytes in the same manner described in U.S. Pat. No. 6,464,849, which was previously incorporated by reference herein.

Figure 7:
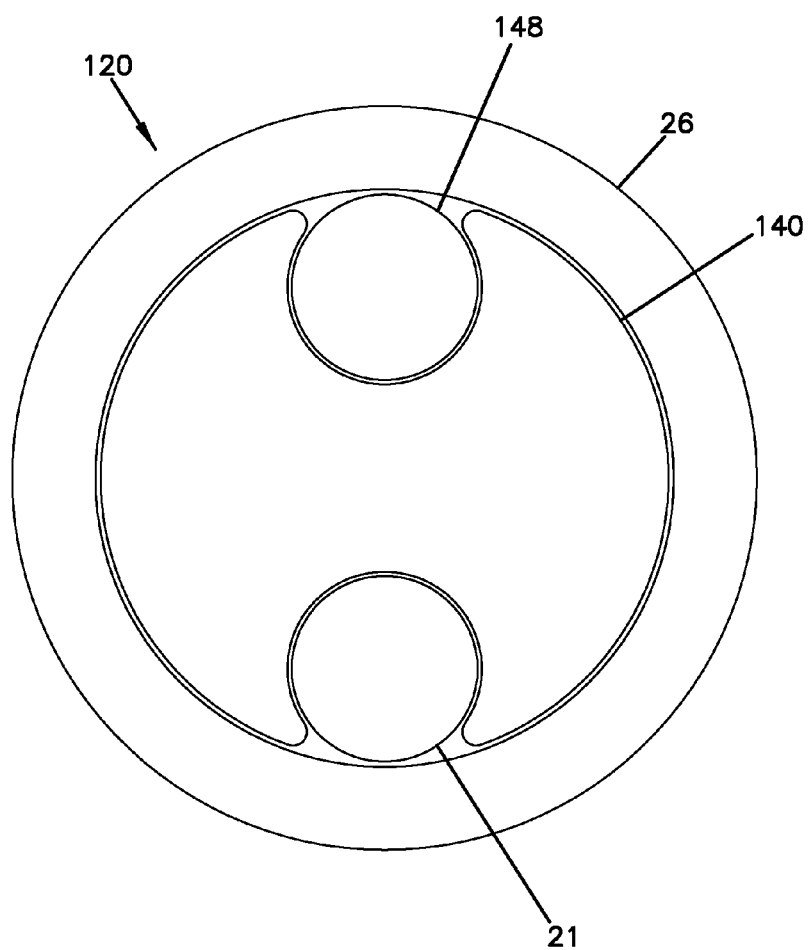
FIG. 7 is an end view showing the sensing tip of a second sensor having features that are examples of inventive aspects in accordance with the principles of the present disclosure.

FIG. 7 shows a second sensor 120 having features that are examples of inventive aspects in accordance with the principles of the present disclosure. The sensor 120 has the same configuration as the sensor of FIGS. 1-4, except a combined counter electrode 148 has been used in place of separate reference and counter electrodes. In certain embodiments, the counter electrode 148 can function only as a counter electrode or as a counter/reference electrode. Also, the sensor 120 has a spacer 140 that has been modified to include only two channels instead of three. The counter/reference electrode 148 can include a material such as silver silver-chloride. The silver silver-chloride can be coated or otherwise provided about the surface of a conductive member such as a wire or fiber (e.g., a composite fiber as described above). In one embodiment, the silver silver-chloride can be incorporated into an outer layer of the wire or fiber.

Figure 8:
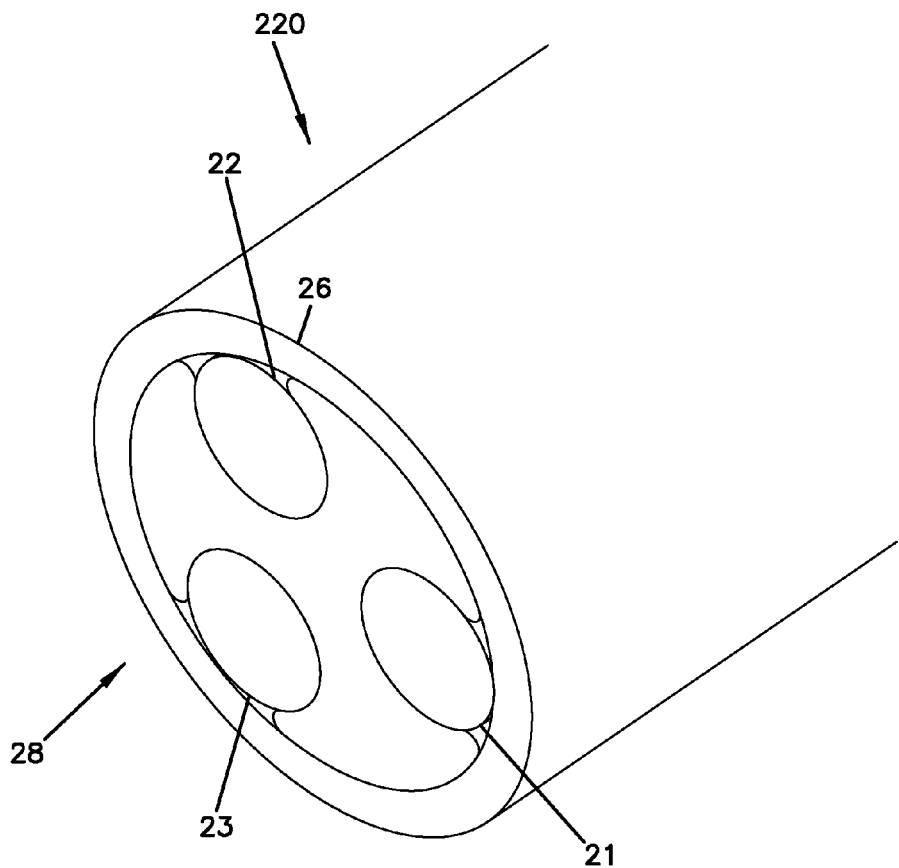
FIG. 8 is a perspective view showing the sensing tip of a third sensor having features that are examples of inventive aspects in accordance with the principles of the present disclosure.

FIG. 8 shows a third sensor 220 having features that are examples of inventive aspects in accordance with the principles of the present disclosure. The sensor 220 has the same construction as the sensor 20 of FIGS. 1-4, except the insulating layer 26 has been extended at the sensing tip 28 to cover and provide mechanical protection for the active ends of the elongated members 21-23. The end of the insulating layer 26 is open to allow a test sample to access the active ends of the elongated members 21-23. The spacer can be use to support the insulating layer 26 and to provide open space/void between the insulating layer 26 and the active surfaces of the elongated members 21-23 such that test fluid can readily reach the active surfaces without obstruction from the sheath 26. For example sufficient space is provided adjacent the active surface of the working electrode to allow the sensing chemistry to rapidly hydrate and to allow analyte desired to be sensed to diffuse into the sensing chemistry.

Figure 9:
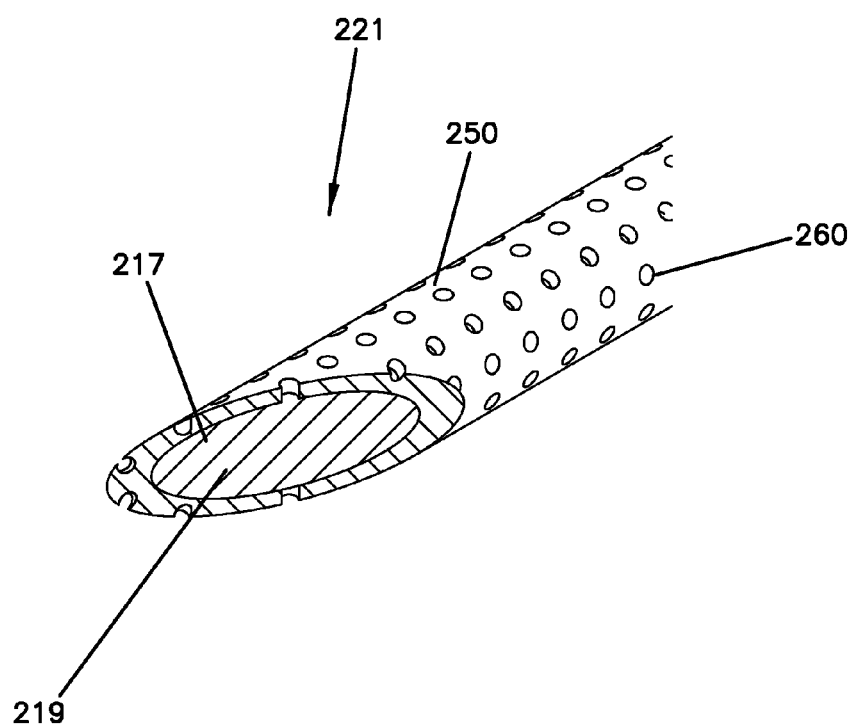
FIG. 9 is a perspective view of a working electrode configuration suitable for use in embodiments in accordance with the principles of the present disclosure.
Figure 10:
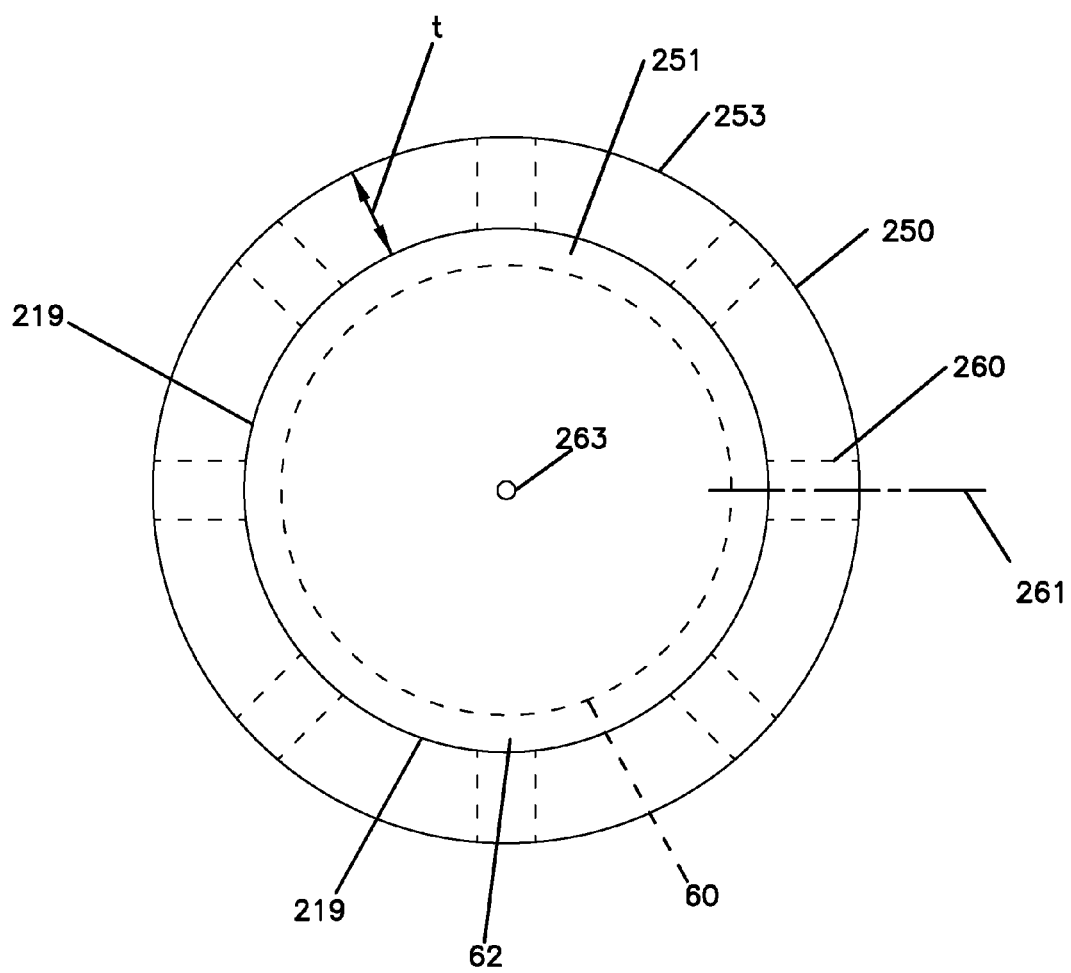
FIG. 10 is an end view of the working electrode configuration of FIG. 9.
Figure 11:
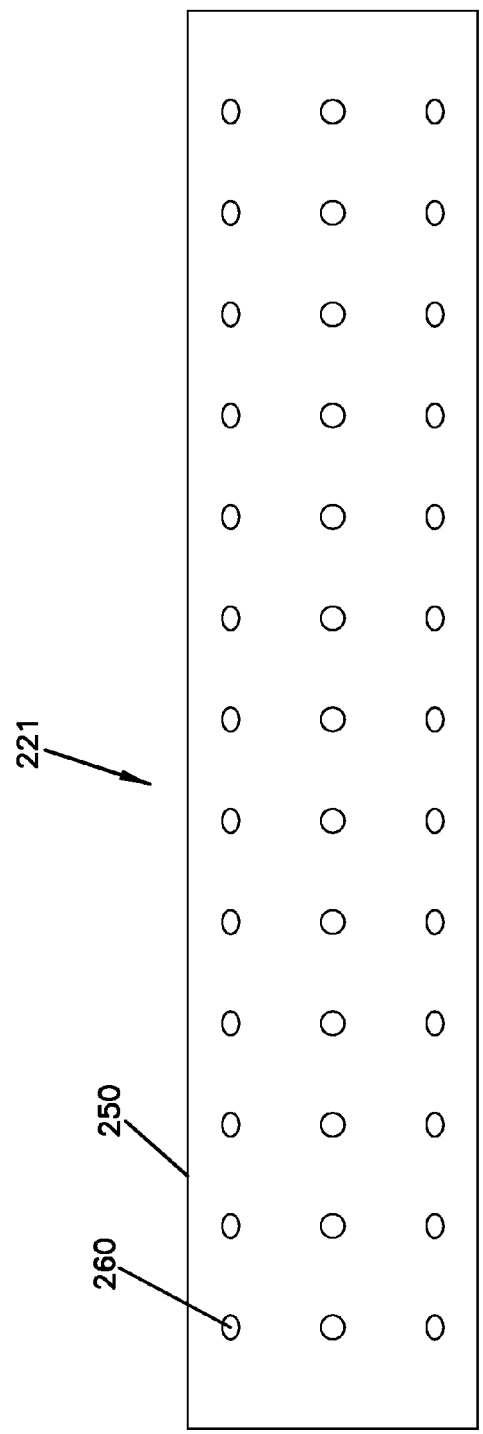
FIG. 11 is a side view of the working electrode configuration of FIG. 9.

FIGS. 9-11 show an elongated member 221 having features that are examples of inventive aspects in accordance with the principles so of the present disclosure. It will be appreciated that the elongated member 221 can be used as a working electrode in any of the above identified embodiments, or in any other type of electro-chemical sensor. The elongated member 221 includes a conductive member 219 (e.g., a conductive wire or fiber as described above) having at least an outer surface or portion that is electrically conductive. In a preferred embodiment, the conductive member 219 has the same construction as the Resistat® composite fiber and includes a dielectric core 60 surrounded by a conductive layer 62. The elongated member 221 also includes a sheath 250 that surrounds the conductive member 219 and extends along the length of the conductive member 219. The sheath 250 defines a thickness t that extends from and inner boundary 251 (e.g., an inner diameter) of the sheath 250 to an outer boundary 253 (e.g., an outer diameter) of the sheath 250. The inner boundary 251 includes an inner surface that engages the outer conductive layer 62 of the conductive member 219. In one embodiment, the inner surface of the sheath 250 is configured to prevent a test sample from moving along the length of the elongated member in the region between the sheath 250 and the conductive member 219. The sheath 250 can also be referred to as an insulating layer, a membrane, a porous layer, a micro-porous layer, or like terms.

Referring still to FIGS. 9-11, the sheath 250 defines a plurality of side openings 260 (i.e., cells, pores, etc.) that extend through the sheath 250 from the inner boundary 251 to the outer boundary 253. In one embodiment, the side openings 260 have central axes 261 that extend in a radial direction relative to a central longitudinal axis 263 of the elongated member 221. In the depicted embodiment, the openings are generally cylindrical in shape. In other embodiments, other opening shapes can be used. In certain embodiments, the openings can have diameters less than or equal to about 100 microns, depths less than or equal to about 100 microns (as defined by the thickness t of the sheath). It will be appreciated that the drawings are schematic and that the number, concentration and size of the openings 260 are for illustration purposes only and are not to scale.

Sensing chemistry 224, such as the sensing chemistry described above, is provided within each of the openings 260. The sensing chemistry 224 within each of the openings 260 is electrically connected to the conductive layer 62 of the elongated member 219.

The openings 260 containing sensing chemistry 224 provide separate working electrode cells that are all electrically connected to the conductive member 219. During testing of a sample, the sensing chemistry is hydrated and a voltage is applied between the working electrode cells and a counter electrode. When the voltage potential is applied, the analyte being sensed reacts with the sensing chemistry at the working electrode cells, and the working electrode cells provide outputs that are combined at the conductive member 219 to cause electrical current to flow through the conductive member 219. This architecture is particularly advantageous when adapted to sensor fabrication related to enzyme sensor chemistries typical to glucose, lactate and other medically important analytes. The architecture allows in-situ fabrication of mass arrayed sensors directly on the surface of canulae or guidewires and makes possible "smart" syringes and various similar devices. It is primarily beneficial to applications requiring implantation, greater micro-miniaturization, or remote placement, and provides manufacturing advantages of improved process, increased throughput, reduced product defects, simplified quality control and quality assurance, and simplification of manufacturing complexity. The architecture also provides mechanical protection of the sensing chemistry and allows for the amount of sensing chemistry exposed to analyte to be accurately controlled. The architecture may also be employed in advanced test strip designs for applications such as glucose monitoring where multiple sensors may be arrayed on single cards or rotating cylinders eliminating the need for patient handling of individual sensor strips for each test. These sensors can use a fraction of the space needed for similar "bandolier" type designs currently on the market and likely produced with lower reject ratios and cost than is now available.

Figure 12:
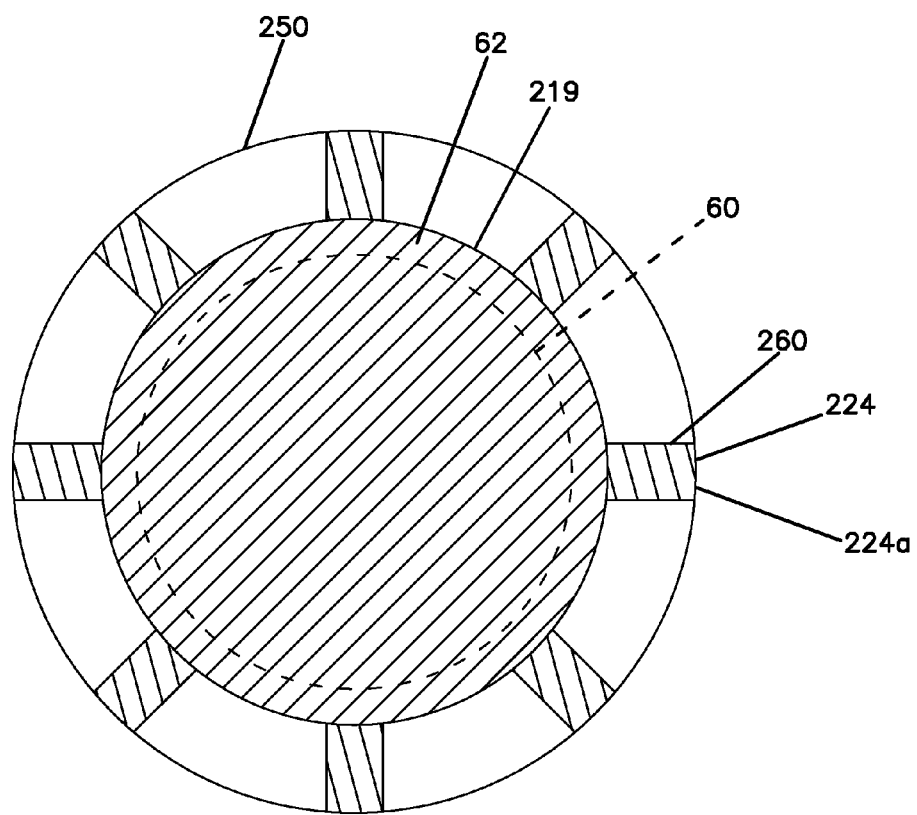
FIG. 12 is a cross-sectional view taken along section line 12-12 of FIG. 11 showing a first sensing chemistry configuration.

FIG. 12 shows an embodiment where the sensing chemistry 224 forms solid rods 224a within the openings 260. In the depicted embodiment, the rods 224a extend outwardly from the conductive member 219 in a radial direction for the full depth of the openings 260 (i.e., for the full thickness of the sheath 250). In other embodiments, the rods 224a can extend outwardly from the conductive member 219 in a radial direction for a partial depth of the openings 260.

For the embodiment of FIG. 12, the sheath 250 can be made of a completely dielectric material such as polycarbonate or other dielectric materials. Alternatively, for the embodiment of FIG. 12, the sheath 250 can also include both dielectric and electrically conductive portions. For example, the sheath 250 can include an inner core portion that is dielectric, and a surface layer that is electrically conductive. The conductive surface layer can include the surface defining the inner boundary 251, the surface defining the outer boundary 253, and the surfaces defining the openings 260. Inherently conductive polymers (ICP) such as doped polyanaline or polypyrrole could be used to form the conductive surface layers of the sheath. Example ICP preparation processes are disclosed at U.S. Pat. No. 5,849,415, which is hereby incorporated by reference in its entirety.

Figure 13:
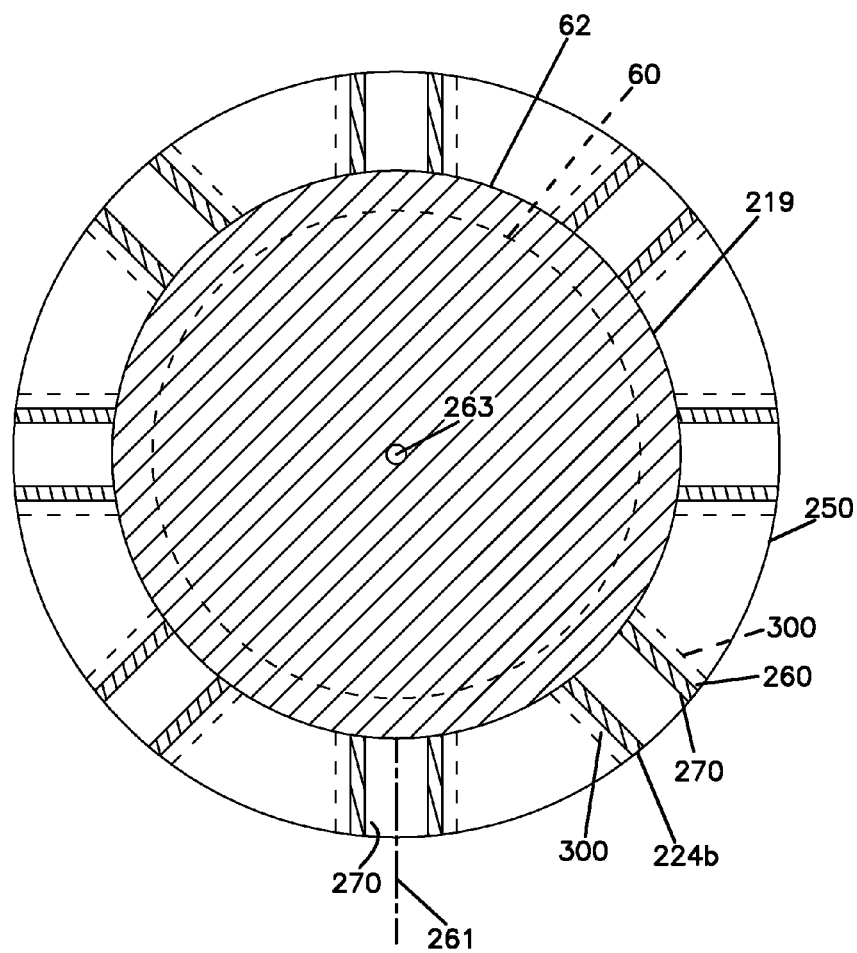
FIG. 13 is a cross-sectional view taken along section line 12-12 of FIG. 11 showing a second sensing chemistry configuration.

FIG. 13 shows an embodiment where the sensing chemistry 224 forms hollow structures 224b (e.g., hollow tubes or cylinders) that line the openings 260. The hollow structures 224b include passages 270 aligned along the central axes 261 of the openings. The hollow structures 224b are electrically connected to the conductive member 219 and extend radially outwardly from the conductive member 219 for at least a portion of the depth of each opening 260. For this embodiment, the sheath 250 preferably includes an inner core portion that is dielectric, and a surface layer that is electrically conductive as described above. For example, it is preferred for the openings 260 to be lined by a conductive layer that surrounds the hollow structures 224b and that provides an electrical pathway for carrying current radially through the sheath 250 between the conductive member 219 and the sensing chemistry 224.

The passages 270 assist in rapidly hydrating the sensing chemistry 224 to improved sensor response times. Also, the size (e.g., the diameter) of the passages can be selected to extend sensor life by controlling/limiting the amount of sensor chemistry that can react with the analyte desired to be sensed at a given time. For example, while the passages 270 can be sized to allow the sensing chemistry to be rapidly hydrated, they can also be sized to allow the analyte being sensed to react only with the outermost sensing chemistry. In one embodiment, the passages have inner diameters less than 100 microns. For example, as the analyte enters the passages 270, the analyte reacts with the portion of the hollow structure 224b located furthest from the conductive member 219 and is consumed before the analyte can migrate further radially inwardly into the passages 270. Over time, the portion of the hollow structure 224b that is furthest from the conductive member 219 is depleted. When this occurs, the analyte is able to move deeper radially into the openings 260 to reach active portions of the hollow structures 260. This process continues until the analyte depletes the entire radial lengths of the hollow structures 224b and the life of the sensor ends. In this progression, the portions of the hollow structures located closest to the conductive member 219 are the last portions of the sensing chemistry to be depleted.

Two manufacturing principles are preferably taken into consideration when forming the openings 260 in the sheath 250. The first is the ability to easily create large arrays of smooth straight pores through a conformable polymer and the second is the ability to regulate both the density of the pore field and the ratio of the pore opening to its depth. To fabricate an elongated member such as the elongated member 221, an elongate conductive member (as described above) is coated along some portion of its length with a thin dielectric film suitable for deep reaction ion etching (DRIE) or other process capable of forming suitable blind passages corresponding to the openings 260.

A first example of a process suitable for the creating the dielectric coating for the sheath is to produce a thin film of Parylene polymer over some portion of the conductive member's length to a thickness of preferably less than ~80 microns. The Parylene coating may be applied using standard commercially available methods whereby the solid phase monomer precursor (monomeric diradical para-xylylene) is heated in a vacuum chamber to produce a vapor. The vapor is next drawn into a coating chamber where the conductive member is exposed to the vapor that condenses uniformly over the outer surface of the conductive member. As used in the coating step here, the vacuum chamber can include air tight entrance and exit glands allowing for a continuous passing of the conductive member into the chamber target area to produce the desired dielectric film along its desired length. Parylene conformal coatings are suitable to DRIB, have relatively low temperature process requirements, and can be controlled in uniform thicknesses from 500 Angstroms to 75 microns to provide consistent, defect free coatings over any geometry without sagging. These characteristics are particularly advantageous to applying coatings over elongate, nonplanar (e.g., cylindrical) substrates.

The minimal negative impacts of the Parylene coating process on target substrates expands the potential for use of many standard commercial grade monofilament polymer threads as conductive members for biosensor applications. For most of these materials a "sputter" coating step may be employed to produce a thin film conductive surface on the monofilament from a noble metal such as gold or platinum rather than the suffusion coating method described above. The resultant metallic thin film is sufficient to provide a suitable substrate for the Parylene coating and act as the conductor. Sputter coating provides the option of specifying various metals and alloys better suited to alternative sensing chemistries. Where sputter coating is desired, the two steps of sputter coating and Parylene coating as well as certain subsequent coatings having such purpose as to pattern electrically differentiated zones for such use as integrated counter/reference electrodes (e.g., counter/reference electrode coating provided at the outer surface of the sheath 250), may be integrated as part of a single continuous manufacturing line in much the same way that insulated co-axial electrical wires are commonly fabricated.

A second example of a potentially suitable process for integrating the sheath 250 onto the conductive member is to dissolve a polycarbonate or polyester resin precursor in a volatile solvent specific to the resin such as methylene chloride, but such solvent remaining harmless to the base material of the conductive member—such as carbon suffused or gold sputter coated nylon discussed earlier that has been specifically treated to accept the particular over-coating uniformly. The resin solute then may be used as a coating bath for a first process step whereby the conductive member travels continuously into one or more baths and is then drawn out vertically at such rate and under such conditions so as to evaporate the solvent between each bath and cause a thin film (e.g., less than 80 microns) of polycarbonate to remain bound to the surface of the conductive member. Recent developments using doped ICP co-polymers to produce aqueous cast films and coatings now commercially available (Panipol, Inc., Cornelius) suggest that such films may be coated directly onto the nylon substrate monofilament either by this process or by passing through an atomized fluid bath Regardless of the particulars of the dielectric coating, the coated conductive member may then be subjected to a next process generally similar to that of DRIE fabrication for flat membranes, except that the coated conductive wire filament sensor substrate is drawn through, or enclosed within, a radiation containment chamber so configured as to expose a portion of the wire circumference to the directed high energy radiation source typical to track etched pore fabrication. The directed energetic particles within the chamber pass fully through the dielectric coating material leaving straight tracks of damaged molecular debris in the dielectric film that are mostly absorbed at the carbonized nylon (or metallic) conductive surface of the conductive member. The damaged material may be then be selectively etched away using another reel to reel process potentially augmented with ultrasonic stirring to create the arrayed analysis cells extending out from the conductive face of the conductive member to the outer distal surface of the dielectric thin film.

After the porous coating has been cleaned and the surface energies reduced by surfactants or corona discharge treatment, the coated conductive member is collected on reels and sent through the chemistry coating station. In this process, the coating station may be either pressurized or put under high vacuum and cooled to near the freezing point of the sensor chemistry in order to facilitate the filling of the micro-sensor array while in the coater. In some embodiments, the sensor chemistry can fill the individual cells completely before exiting the coating station and the excess chemistry wiped clean of the exposed outer surface of the dielectric coating by a sealing gland upon exit. The conductive member then enters the curing station where partial vacuum and/or reduced humidity and slightly elevated temperature cause the volatile components of the sensor chemistry to escape to atmosphere. The sensor chemistry should either be formulated to dry within the cell with the residue substantially filling the void after curing or be dried to a thin film coating the walls of the cell, but leaving an open channel concentric to the pore diameter, passing substantially to the bottom of the cell at the conductor interface to facilitate hydration.

If it is desired to provide the sheath 250 with a conductive surface, as described above, additional processing steps preceding the sensor chemistry deposition can be used to create a secondary conductive layer at least lining the inner wall of the analysis cell. The preferred method would use the ICP co-polymer aqueous solution to cast the DRIE process-able porous layer which would yield cells inherently semi-conductive and bound electrically to the highly conductive output connector surface of the monofilament. Alternatively, one of several available ICP preparation processes (see U.S. Pat. No. 5,849,415) combining the steps of chemically functionalizing the porous substrate and creating molecular attachments to the ICP polymer would be employed to create the required conductive surface domain receptive to the sensing chemistry. Once created and filled with sensor chemistry the individual nano analysis cells would then function as working electrodes with the thickness of the porous substrate in part determining the service life of the sensor. A non ICP coating process for plastics using an aqueous suspension of carbon nanotubes has been developed by Eikos Inc. referred to as Nanoshield™. This process offers similar thin film conductive properties. Relatively high conductivities are reported for the Nanoshield process providing surface films without substantial dimensional changes to the substrate dimension.

Following the required coating and curing steps specific to the agents selected, the sensors fabricated using the in situ process of porous layer fabrication are functionally complete and do not need any outer protective component. For most in-vivo applications however, a final biocompatible layer can be used to provide an anti thrombogenic surface to protect the micro-array field from the body's damaging immune responses. Following this process the completed sensor may enter any number of secondary operations where it can be configured for use directly in catheters, syringes, or tissue as needed by the specific application.

Many prior art enzymatic sensor designs considered as candidates for minimally invasive diagnostics suffer from trade-offs made in miniaturizing the structure adequately for non-surgical short term implantation. Despite their proven advantages of low cost, and relatively simple function that are important characteristics needed for all disposable diagnostics, the use of organic sensing chemistry and historical process techniques dependent on flat structures make achieving the goal of highly repeatable and reliable sensors that are also minimally invasive elusive. Enzymatic sensors typically require a layered structure that generally includes an entry port, some means to move the analyte into the sensor and a central chamber having the sensor chemistry where the analysis is done. The high precision required in maintaining an accurate and repeatable relationship among the functional elements of the device is dependent on processes such as screen printing, die cutting and droplet deposition that although are easily achieved for in-vitro devices often limit the degree to which these sensors can be micro-miniaturized.

The demand for smaller and smaller disposable sensors capable of residing in tissue, organs or vasculature without interference to the biological process or discomfort to the patient is likely to drive the flat sensor design beyond the practical limit of the most cost effective manufacturing processes. Paradoxically, while the theoretical size of the active analysis surface needed to produce a useful electrical signal has continued to shrink to the point where a practical enzymatic glucose analysis can occur on the tip of a human hair ~80 microns diameter, the typical planar construction package based on laminar films and able to support that analysis has a minimum single surface dimension greater than ~1000 microns, most of which is required for tolerance allowances and bond pads. Certain inventive aspects disclosed herein are adapted to provide new structures that can leverage the full miniaturization potential of enzymatic sensors while providing both significantly lower costs and the high reliability demanded by implantable diagnostics.

In certain embodiments in accordance with the principle so of the present disclosure, a DRIE active film is cast in-situ on the conductive output surface of a conductive member along with the etched pathways of a pore field forming mass arrayed nano analysis cells. In function, the target analyte flux diffuses into each cell and is converted by the resident sensor chemistry to a proportional current collected at the floor of the cell by the common conductive output of the conductive member. The design and control of the DRIE film thickness, the density of the pore field, the ratio of the pore aperture to the area of its reactive surface within the analysis cell, and the surface energy of its walls are all highly predictable. Such abilities may be used in the fabrication of biochemical sensors to affect a wide range of sensor response characteristics including: life cycle, sensitivity, rise time, hydration time, and interferent response becoming inherent properties of the cast film rather than as independent external variables. This control is predicted by the highly ordered and relatively static environment of the sensor chemistry (e.g., hydrogel) within the nano analysis cells that is not possible to achieve in the dynamic macro environment of assembled laminar membranes and conductors separated by gel matrices typical to planar enzymatic sensor technology. In addition to controlling the physical characteristics of the analysis cells, the sensor chemistry physical properties may also be optimized to control parameters such as viscosity, residual moisture, cured film thickness, etc. and then related to the specific nano cell properties to further define performance and coating integrity. By creating a fixed and integral membrane, cast in place on the conductive member, the sensor becomes a unified structure more robust and with greater reliability and reduced susceptibility to issues such as mechanically induced electronic noise resulting from the dynamic environment of living tissue. For certain embodiments of the present disclose, the potential for miniaturization down to diameters <200 microns is achievable for wired enzyme type diagnostic sensors and it may be anticipated that enzymatic biosensor constructions can be fabricated for commercial use that will be within the dimensional footprint of competitive solid state and optical sensors at substantially lower market entry costs. Biosensors having these new capabilities that are producible at high volume and low cost may allow the development of a new generation of continuous sensors for minimally invasive clinical diagnosis and monitoring of relevant biomarkers such as glucose, lactate and other medically significant molecules in humans.

From the foregoing detailed description, it will be evident that modifications and variations can be made without departing from the spirit or scope of the broad inventive aspects embodied in the embodiments disclosed herein. For example, any of the embodiments disclosed herein can use separate reference and counter electrodes instead of combined counter/reference electrodes.

What is claimed is:
1. A sensor for sensing an analyte in a sample comprising:
an outer member that is elongated along a longitudinal axis;
a spacer positioned within the outer member, the spacer defining first and second channels having lengths that extend along the longitudinal axis, the channels further having open longitudinal sides facing outwardly toward the outer member;
a first elongated member positioned within the first channel, the first elongated member defining a working electrode having a sensing layer; and
a second elongated member positioned within the second channel, the second elongated member defining a counter electrode, a reference electrode, or a combined reference and counter electrode;
the spacer being sized and configured to separate the first elongated member from the second elongated member and to provide open space extending along the longitudinal axis between the outer member and the first and second elongated members through which a test sample can flow, the sensing layer having an axial length that extends along a corresponding axial length of the spacer so that the sensing layer is accessible within the open space, thereby enabling the sensing layer to be wetted along its axial length by the test sample as the test sample moves longitudinally through the open space.

2. The sensor of claim 1, wherein the second elongated member defines a counter electrode; and wherein the spacer further defines a third channel in which a third elongated member is positioned, the third elongated member defining a reference electrode.

3. The sensor of claim 1, wherein active surfaces of the elongated members project outwardly from the outer member and face radially outwardly from the channels of the spacer.

4. The sensor of claim 3, wherein the outer member extends around the active surfaces and defines an open end to facilitate access to the active surfaces.

5. The sensor of claim 1, wherein the spacer is constructed of a dielectric material.

6. The sensor of claim 1, wherein the first elongated member includes a dielectric core surrounded by a conductive layer, which is covered by the sensing layer.

7. The sensor of claim 1, wherein each elongated member includes a composite nylon monofilament conductive thread material.

8. The sensor of claim 1, wherein the outer member includes an insulating sheath.

9. A sensor for sensing an analyte in a sample comprising:
an outer member that is elongated along a longitudinal axis;
a spacer positioned within the outer member, the spacer defining a channel having a length that extends along the longitudinal axis, the channel further having an open longitudinal side facing outwardly toward the outer member;
a first elongated member positioned within the channel, the first elongated member defining a working electrode having a sensing layer;
the spacer being sized and configured to provide open spacing extending along the longitudinal axis between the outer member and the sensing layer of the working electrode through which a test sample can flow, the sensing layer having an axial length that extends along a corresponding axial length of the spacer, and the sensing layer being wetted along its axial length by the test sample as the test sample moves longitudinally through the open spacing.

10. The sensor of claim 9, wherein an active surface of the first elongated member projects outwardly from the outer member and faces radially outwardly from the channel of the spacer.

11. The sensor of claim 10, wherein the outer member extends around the active surface and defines an open end to facilitate access to the active surface.

12. The sensor of claim 9, wherein the spacer is constructed of a dielectric material.

13. The sensor of claim 9, wherein the first elongated member includes a dielectric core surrounded by a conductive layer, which is covered by the sensing layer.

14. The sensor of claim 9, wherein the first elongated member includes a composite nylon monofilament conductive thread material.

15. The sensor of claim 9, wherein the outer member includes an insulating sheath.

* * * * *